United States Patent [19]
Misselbrook et al.

[11] Patent Number: 5,317,004
[45] Date of Patent: May 31, 1994

[54] MICROENCAPSULATED YELLOW POLYMORPHIC FORM OF TRIFLURALIN

[75] Inventors: John Misselbrook, Lawrenceville, N.J.; Larry J. McKinney, Hahira, Ga.; James H. Lefiles, Valdosta, Ga.; Edwin F. Hoff, Jr., Valdosta, Ga.; Elliot Bergman, Valdosta, Ga.

[73] Assignee: Griffin Corporation, Valdosta, Ga.

[21] Appl. No.: 974,674

[22] Filed: Nov. 12, 1992

Related U.S. Application Data

[60] Continuation of Ser. No. 873,584, Apr. 21, 1992, abandoned, which is a continuation of Ser. No. 750,773, Aug. 22, 1991, abandoned, which is a continuation of Ser. No. 568,509, Dec. 10, 1990, abandoned, which is a division of Ser. No. 301,458, Jan. 24, 1989, Pat. No. 5,160,530.

[51] Int. Cl.$^5$ .................. A01N 25/28; A01N 33/08
[52] U.S. Cl. .................. 504/116; 504/347; 71/DIG. 1
[58] Field of Search .................. 504/347, 116

[56] References Cited

U.S. PATENT DOCUMENTS

| | | | |
|---|---|---|---|
| 3,257,190 | 6/1966 | Soper | 71/2.3 |
| 4,150,969 | 4/1979 | Dudkowski | 71/121 |

Primary Examiner—Allen J. Robinson
Assistant Examiner—S. Mark Clardy
Attorney, Agent, or Firm—Jones & Askew

[57] ABSTRACT

Agriculturally active materials, such as pesticides, herbicides and the like and a process for microencapsulating said materials. The present invention includes trifluralin having a polymorphic form characterized by a yellow color and a melting point of approximately 41°–43° C. The present invention also includes a method of using the yellow polymorphic form of trifluralin as a herbicide. In addition, the present invention includes a method of microencapsulating low-melting agriculturally active materials, such as trifluralin. The microencapsulation process comprises the steps of heating a low-melting, water-immiscible, agriculturally active material to a molten state. The molten active material is then combined with an aqueous solution of a water-soluble, film-forming polymer at a temperature sufficient to maintain the active material in its molten state. The active material is then dispersed or emulsified in the aqueous solution so that the active material has a primary particle size of between approximately 0.1 and 10 microns. The resulting dispersion or emulsion is then spray dried at a temperature between approximately 50° and 220° C. so as to microencapsulate the active material in the polymer. Compounds for promoting the rapid solidification of the active material are also disclosed.

7 Claims, 5 Drawing Sheets

- 0.5-10 MICRONS DROPLETS
- PVA WALL
- VOID
- TRIFLURALIN
- 25-200 MICRONS

MICROENCAPSULATED YELLOW POLYMORPHIC FORM OF TRIFLURALIN

This is a continuation of application Ser. No. 07/873,584 filed Apr. 21, 1992, now abandoned, which is a continuation of application Ser. No. 07/750,773, filed Aug. 22, 1991, now abandoned, which is a continuation of application Ser. No. 07/568,509, filed Dec. 10, 1990, now abandoned, which is a division of application Ser. No. 07/301,458, filed Jan. 24, 1989 now U.S. Pat. No. 5,160,530.

FIELD OF THE INVENTION

The present invention relates generally to microencapsulated agriculturally active materials, such as pesticides, herbicides and the like, and to a process for producing said microencapsulated materials. More particularly, the present invention relates to a microencapsulated polymorphic form of trifluralin and other herbicides displaying two or more polymorphic forms and to a process for making and using the same. The present invention also relates to a process for microencapsulating low-melting agriculturally active materials, to crystallization initiators and stabilizers for said agriculturally active materials and to a process for reducing nitrosamine impurities while microencapsulating agriculturally active materials containing nitrosamines.

BACKGROUND OF THE INVENTION

Agriculturally active materials, such as pesticides, herbicides and the like, are widely used throughout the agricultural industry. For convenience in packaging and handling, such agriculturally active materials are typically produced in the form of a dry solid, such as a powder, which can be readily mixed with water. The aqueous solution or dispersion of the active material is then typically applied to an area to be treated by spraying.

In order to produce aqueous solutions or dispersions suitable for application by spraying, the agriculturally active material must be in a form which can be readily incorporated with water. The agriculturally active material by itself, however, is usually insoluble in water or has an unacceptably low water solubility. Therefore, it is usually necessary to treat the agriculturally active material in some manner to enhance its combinability with water.

One such method of treating agriculturally active materials is microencapsulation. For example, U.S. Pat. No. 4,280,833 discloses a process for microencapsulating water-immiscible materials, such as herbicides, and, specifically, trifluralin. The microencapsulation process involves an aqueous phase containing an emulsifier and an organic phase. The organic phase consists of a water-immiscible material, such as trifluralin, and polymethylene polyphenylisocyanate. The organic phase is added to the aqueous phase with agitation to form a dispersion of small droplets of the organic phase within the aqueous phase. Thereafter, a polyfunctional amine is added to the dispersion. The polyfunctional amine reacts with the isocyanate to form a capsular polyurea shell about the herbicide droplet. This type of microencapsulation process is termed interfacial polycondensation. Other patents which involve microencapsulation by polycondensation processes include U.S. Pat. Nos. 4,360,376; 4,417,916; 4,563,212; 3,429,827; 3,577,515; 3,959,464 and 4,640,709.

Another process used to microencapsulate active materials is spray drying. U.S. Pat. No. 4,244,836 relates to a microencapsulation process using spray drying. In that process, a liquid, water-insoluble phase is dispersed in an aqueous phase. The liquid, water-insoluble phase can be materials, such as plant protecting agents. The aqueous phase is a water-soluble polyvinyl alcohol solution. The water-insoluble phase is dispersed in the aqueous phase using a stirrer or a homogenization device so as to produce droplets of the water-insoluble phase of from 1 to 50 microns in diameter within the aqueous phase. The dispersion in then atomized into a stream of heated air (spray dried). The spray drying dehydrates the aqueous dispersion and produces a dry powdery microcapsular product. Other patents which utilize a spray drying technique for microencapsulation include U.S. Pat. Nos. 4,286,020; 4,353,962 and 4,690,786.

Active materials which can be microencapsulated include plant protecting agents, such as herbicides. Many conventional herbicides, particularly dinitroaniline-based herbicides, contain nitrosamine impurities. Since nitrosamines are recognized carcinogens and since current governmental regulations limit the amount of nitrosamines which herbicides can contain, it is desirable to reduce the level of nitrosamines present in herbicides, particularly trifluralin. Various methods are known for reducing the level of nitrosamine impurities in herbicides as shown in U.S. Pat. Nos. 4,335,260; 4,338,473; 4,440,962; 4,501,608; and 4,537,992. These known methods of reducing nitrosamine contamination, however, typically involve relatively costly and complicated chemical processes. Accordingly, a relatively simple, effective and inexpensive method for reducing nitrosamine impurities in herbicides has long been sought.

Some herbicides are known to exist in two or more polymorphic forms. For example, U.S. Pat. No. 4,082,537 discloses that N-(1-ethylpropyl)-2,6-dinitro-3,4-xylidine [also known as N-(1-ethylpropyl)-3,4-dimethyl-2,6-dinitrobenzenamine] exists in two distinct polymorphic forms: a yellow microcrystalline form and an orange macrocrystalline form. The yellow polymorph, although considered less stable than the orange polymorph, has the advantage of being slower to settle out of aqueous dispersions, such as those involved with spraying equipment. The yellow polymorph is found in freshly prepared N-(1-ethylproply)-2,6-dinitro-3,4-xylidine which slowly converts to the orange polymorph with age. However, when sodium dioctyl sulfosuccinate is added to molten N-(1-ethylpropyl)-2,6-dinitro-3,4-xylidine followed by cooling, solidification and conversion to a wetable powder, the compound produces stable aqueous dispersions of the yellow polymorph. The production of herbicidal dispersions which are more stable than the known herbicidal dispersions is therefore desirable.

SUMMARY OF THE INVENTION

Generally speaking, the present invention relates to herbicidal compositions in a desired polymorphic form and to a process for microencapsulating said herbicidal compositions. More particularly, the present invention includes a herbicidal composition comprising alpha, alpha, alpha-trifluoro-2,6-dinitro-N,N-di-n-propyl-p-toluidine (trifluralin) having a polymorphic form characterized by a yellow color and a melting point of approximately 41°–43° C. The present invention also includes a method of using the yellow polymorphic form of trifluralin as a herbicide. In addition, the present invention includes a method of microencapsulating low-melting agriculturally active materials, such as trifluralin. The microencapsulation process comprises the steps of heating a low-melting, water-immiscible, agriculturally active material to a molten state. The molten active material is then combined with an aqueous solution of a water-soluble, film-forming polymer at a temperature sufficient to maintain the active material in its molten state. The active material is then dispersed or emulsified in the aqueous solution so that the active material has a primary particle size of between approximately 0.1 and 10 microns. The resulting dispersion or emulsion is then spray dried at a temperature between approximately 50° and 220° C. so as to microencapsulate the active material in the polymer.

In one aspect of the invention, the active material which is microencapsulated is the yellow polymorphic form of trifluralin (alpha, alpha, alpha-trifluoro-2,6-dinitro-N,N-di-n-propyl-p-toluidine). In another aspect of the invention, the active material which is microencapsulated is selected from the group consisting of N-(1-ethylpropyl)-3,4-dimethyl-2,6-dinitrobenzenamine; 3,5-dibromo-4-hydroxybenzonitrile octanoate; 4-hydroxy-3,5-diiodobenzonitrile octanoate and methyl-N,N-dimethyl-N-[(methylcarbomyl)oxy]-1-thiooxamimidate.

In an alternate embodiment, the invention comprises a method of microencapsulating a desired polymorphic form of a high-melting agriculturally active material. The microencapsulation process comprises the steps of grinding a high-melting, water-immiscible active material to a primary particle size of between approximately 0.1 and 10 microns. The ground active material is then combined with an aqueous solution of a water-soluble, film-forming polymer such that said active material is dispersed or emulsified in said aqueous solution. The resulting dispersion or emulsion is then spray dried at a temperature between about 50° and 220° C. so as to microencapsulate the active material in the polymer. In one aspect of the invention, the active material is tetrachloroisophthalonitrile (chlorothalonil). In another aspect of the invention, the active material is 2-chloro-4-ethylamino-6-isopropylamino-s-triazine (atrazine).

Another embodiment of the invention comprises a method of reducing nitrosamine impurities in herbicides. The method comprises the steps of dispersing or emulsifying a water-immiscible, nitrosamine-containing herbicide in an aqueous solution of a film-forming polymer such that said dispersed or emulsified herbicide has a particle size between approximately 0.1 and 10 microns. The resulting dispersion or emulsion is then spray dried at a temperature between about 50° and 220° C. so as to microencapsulate the herbicide in the polymer, whereby the amount of nitrosamine in said microencapsulated herbicide is reduced. In one aspect of the invention, the active material is trifluralin.

Another embodiment of the invention comprises a method for producing a desired polymorphic form of active materials which exhibit two or more heat-alterable polymorphic forms. The method comprises the steps of heating to a molten state a water-immiscible active material which exhibits two or more heat-alterable polymorphic forms, the active material being in one polymorphic state prior to heating. The molten active material is then combined with an aqueous solution of a water-soluble, film-forming polymer at a temperature sufficient to maintain the active material in the molten state. The active material is then dispersed or emulsified in the aqueous solution so that the active material has a primary particle size of between approximately 0.1 and 10 microns. The resulting dispersion or emulsion is then spray dried so as to microencapsulate the active material in the polymer. The microencapsulated active material is then cooled to a temperature below the melting point of the active material, whereby the microencapsulated active material is in another polymorphic form.

Accordingly, it is an object of the present invention to provide improved agriculturally active compositions.

Another object of the present invention is to provide a method of using as herbicides the desired polymorphic form of herbicides, particularly trifluralin.

A further object of the present invention is to provide an improved method of microencapsulating low-melting agriculturally active materials.

An additional object of the present invention is to provide an improved method of microencapsulating trifluralin.

Yet another object of the present invention is to provide herbicides having improved stability.

Another object of the present invention is to provide trifluralin in a solid, free-flowing form.

Still another object of the present invention is to provide polymorphic herbicides in a form having improved biological activity.

Another object of the present invention is to provide microencapsulated agriculturally active materials which are capable of being cycled from a solid form, through the melting point of the active material and back to a solid form.

A further object of the present invention is to provide an improved method of microencapsulating high-melting agriculturally active materials.

Another object of the present invention is to provide an improved method of reducing nitrosamine impurities in herbicides.

An additional object of the present invention is to provide a method of converting agriculturally active materials from one polymorphic form to another and maintaining or preserving the active material in the other polymorphic form.

These and other objects, features and advantages of the present invention will become apparent after a review of the following detailed description of the disclosed embodiments and the appended claims.

DETAILED DESCRIPTION OF THE DISCLOSED EMBODIMENTS

The invention relates to microencapsulation of agriculturally active materials, such as herbicides, insecticides, fungicides, nematicides, miticides and plant growth regulators. The agriculturally active materials useful in the present invention can generally be grouped into two types of compounds: low-melting and high-melting. Low-melting agriculturally active materials are generally those which have melting points below approximately 130° C.; high-melting agriculturally active materials are generally those which have melting points above approximately 130° C. These agriculturally active materials are also solid under ambient or room temperature conditions (approximately 20° C.).

One disclosed embodiment of the present invention involves a process for the microencapsulation of low-melting agriculturally active materials. In this low-melting process, the chemical nature of the agriculturally active material is generally not critical. With respect to physical properties, the agriculturally active material must be substantially immiscible with water and, of course, must be low-melting as defined above. The agriculturally active material must also be substantially inert with respect to the material which forms the microcapsule wall, as will be described further hereinbelow.

The low-melting microencapsulation process is performed by first providing an aqueous solution of a water-soluble, film-forming polymer. The low-melting, agriculturally active material is then heated to a temperature above its melting point so that the normally solid material becomes liquid. The molten active material is then combined with the aqueous phase. The temperature of the aqueous phase must be such that when the molten active material is added thereto, the molten active material remains molten. Generally speaking, therefore, the temperature of the aqueous phase must be at or above the melting point of the active material. The active material is then dispersed or emulsified in the aqueous phase by vigorous agitation or mixing with appropriate apparatus well known in the art, such as high shear mixers or homogenizers. The objective of this dispersing or emulsifying step is to convert the molten active material into a plurality of tiny liquid droplets uniformly dispersed in the aqueous phase. Accordingly, the dispersing or emulsifying step should be conducted so as to provide droplets of liquid active material having a primary particle size of between approximately 0.1 and 10 microns; preferably, between approximately 0.8 and 2.0 microns.

Figure 1:
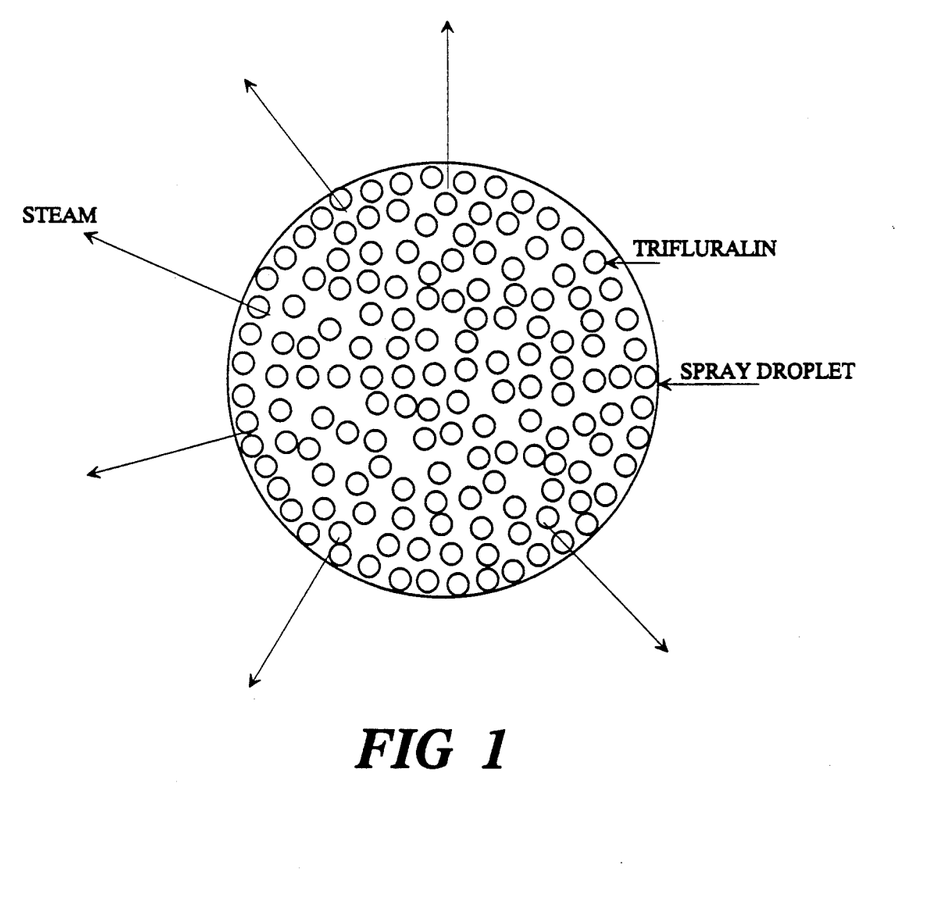
FIG. 1 is a simplified graphic illustration of the dehydration of an emulsion droplet.
Figure 2:
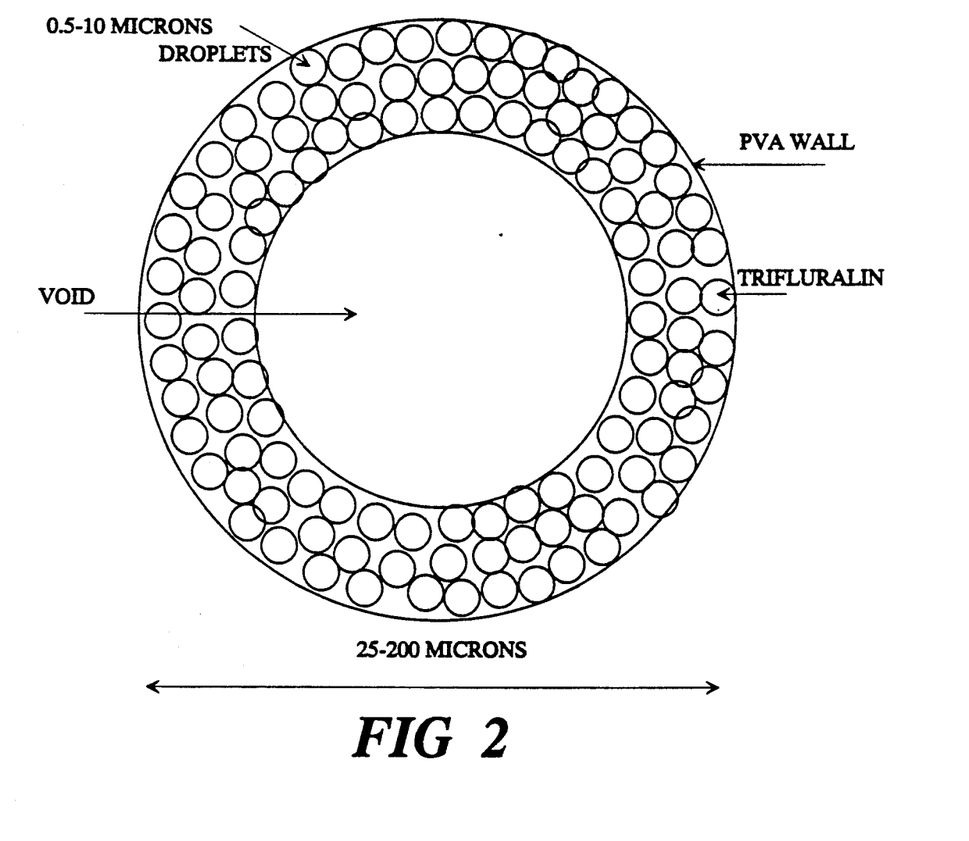
FIG. 2 is a simplified graphic illustration of the emulsion droplet of FIG. 1 after drying showing encapsulated trifluralin.

The resulting dispersion or emulsion of the active material in the aqueous phase is then spray dried using conventional spray drying equipment which is well known to those skilled in the art. The purpose of spray drying the dispersion or emulsion is to dehydrate it (FIG. 1) and thereby form a capsule wall of the film-forming polymer around the droplets of active material. In order to accomplish this dehydration step, the dispersion or emulsion is spray dried at a temperature between approximately 50° and 220° C. In terms of conventional spray drying equipment, the spray drying should be conducted using an air inlet temperature of between approximately 110° and 220° C.; preferably, between approximately 180° and 200° C. An air outlet temperature of between approximately 50° and 120° C.; preferably, between approximately 90° and 110° C. is used. The spray drying process produces dry, free-flowing product containing the active material. The free-flowing product containing the active ingredient formed by the spray drying process will generally have a particle size of between approximately 10 and 500 microns. (FIG. 2).

As stated above, the chemical nature of the low-melting, agriculturally active material is generally not critical to the low-melting microencapsulation process. Examples of low-melting, agriculturally active materials which can be used in the present invention are as follows: Senoxan, Cycloxydim, Chloropropham, Diclofop-Methyl, Alachlor, Fluchloralin, Bromoxynil Octanoate Ester, Ioxynil Octanoate Ester, Trifluralin, Pendimethalin, Cyometrinil, Ethalfluralin, Benfluralin, Oxyfluorfen, Ethofumesate, Flamprop-Isopropyl, Napropamide, Benazolin (ester), Monolinuron, Flamprop-Methyl, Bifenox, Fenoxaprop-Ethyl, Propham, Oxadiazon, Mecoprop, Propanil, Prometon, Quizalofop-ethyl, Linuron, Isocarbamid, Metobromuron, Chlorobromuron, Dazomet, Neburon, Terbutryn, Chlomethoxynil, Hexazinone, Dichloroprop, MCPA, Prometryn, Carbetamide, Methabenzthiazuron, Desmedipham, Methazole, Terbumeton, Prodiamine, Metribuzin, Quinalphos, Butocarboxim, Permethrin, EPN, Methidathion, Chlorpyrifos, Phosalone, Dimethoate, Methamidophos, Fenpropathrin, Salithion, Fenoxycarb, Azinphos-Ethyl, Cypermethrin, Tetramethrin, Azinphos-Methyl, MTMC, Methomyl, Xylylcarb, Cloethocarb, Trichlorfon, Acephate, Amitraz, MIPC, Propoxur, Aminocarb, Aldicarb, Deltamethrin, Trimethacarb, Dioxacarb, Methiocarb, Bendiocarb, Vamidothion, Oxamyl and Hexythiazox.

The amount of active material which is added to the aqueous phase is not especially critical but is generally between approximately 5% and 75% by weight; preferably, between approximately 30% and 50% by weight. The aqueous phase comprises a solution of between approximately 1% and 50% by weight; preferably, between approximately 5% and 20% by weight, of a water-soluble, film-forming polymer. When the foregoing concentrations of active material and film-forming polymer are used, the active material represents between approximately 10% and 90% by weight; preferably between approximately 50% and 90% by weight, of the finished microencapsulated product.

The water-soluble, film-forming polymers which can be used in connection with the present invention are not especially critical. Any suitable water-soluble, film-forming polymer can be used. Examples of water-soluble, film-forming polymers which can be used are: polyvinyl alcohol, polyvinylpyrrolidone, starches, modified starches, alginates, hydroxyalkylcellulose, hydroxyalkylcellulose derivatives, poly (acrylic acid), and homologs and salts thereof, polyacrylamide, natural gums, such as gum arabic, dextrins and proteins, such as gelatin and casein. A particularly useful water-soluble, film-forming polymer is polyvinyl alcohol having a degree of hydrolysis of between approximately 75% and 99%; preferably, between approximately 85% and 90%, and a molecular weight of between approximately 10,000 and 100,000; preferably, between approximately 10,000 and 30,000.

Additives to modify the nature of the microcapsule polymer wall can also be added to the aqueous phase. Examples of such additives are plasticizers, wetting agents and anticaking agents.

As a part of the present invention, it has been discovered that certain agriculturally active materials exist in more than one polymorphic form one of which has preferred properties. These active materials generally exist in one polymorphic form in their natural state. This natural state is usually the more stable polymorphic form. Some of these active materials can be changed from the more stable polymorphic form to another less stable polymorphic form by heating the active material and then cooling to produce the desired form. Generally, heating the active material to a temperature above its melting point will convert at least a portion of the active material from the stable polymorphic form to a less stable polymorphic form upon resolidification. A higher degree of conversion is obtained, however, if the active material is properly cooled from its molten form. In addition, it has been discovered that an additional heat treatment slightly above the melting point of the active material produces, on solidification, a higher degree of conversion to the less stable polymorphic form.

Agriculturally active materials which have been discovered to exist in two or more polymorphic forms include: alpha, alpha, alpha-trifluro-2, 6-dinitro-N,N-di-n-propyl-p-toluidine; N-(1-ethylpropyl)-3,4-dimethyl-2,6-dinitrobenzenamine; tetrachloroisophthalonitrile, 2-chloro-4-ethylamino-6-isopropylamino-S-triazine, 4-hydroxy-3,5-diiodobenzonitrile octanoate; and methyl-N,N-dimethyl-N-[(methylcarbamoyl)oxy]-1-thiooxamimidate. Of the foregoing active materials, all are low-melting, water-immiscible agriculturally active materials except tetrachloroisophthalonitrile and 2-chloro-4-ethylamino-6-isopropylamino-S-triazine which are high-melting. The following table lists the above-referenced active materials and the color and melting points of both their polymorphic forms.

TABLE 1

| Active Material | Stable Polymorph | | Less Stable Polymorph | |
|---|---|---|---|---|
| | Color | Melting Point (°C.) | Color | Melting Point (°C.) |
| alpha, alpha, alpha-trifluoro-2,6-dinitro-N,N-di-n-propyl-p-toluidine | orange | 46°–49° | yellow | 41°–43° |
| N-(1-ethylpropyl)-3,4-dimethyl-2,6-dinitrobenzenamine; | orange | 56°–59° | yellow | 52°–55° |
| tetrachloroisophthalonitrile, | white | 250°–251° | white | 247°–248° |
| 4-hydroxy-3,5-diiodobenzonitrile octanoate; | tan | 57°–59° | tan | 53°–56° |
| methyl-N,N-dimethyl-N-[(methylcarbamoyl)oxy]-1-thiooxamimidate | white | 108°–110° | white | 100°–102° |
| 2-chloro-4-ethylamino-6-isopropylamino-s-triazine | white | 182°–185° | white | 174°–178° |

Figure 3:
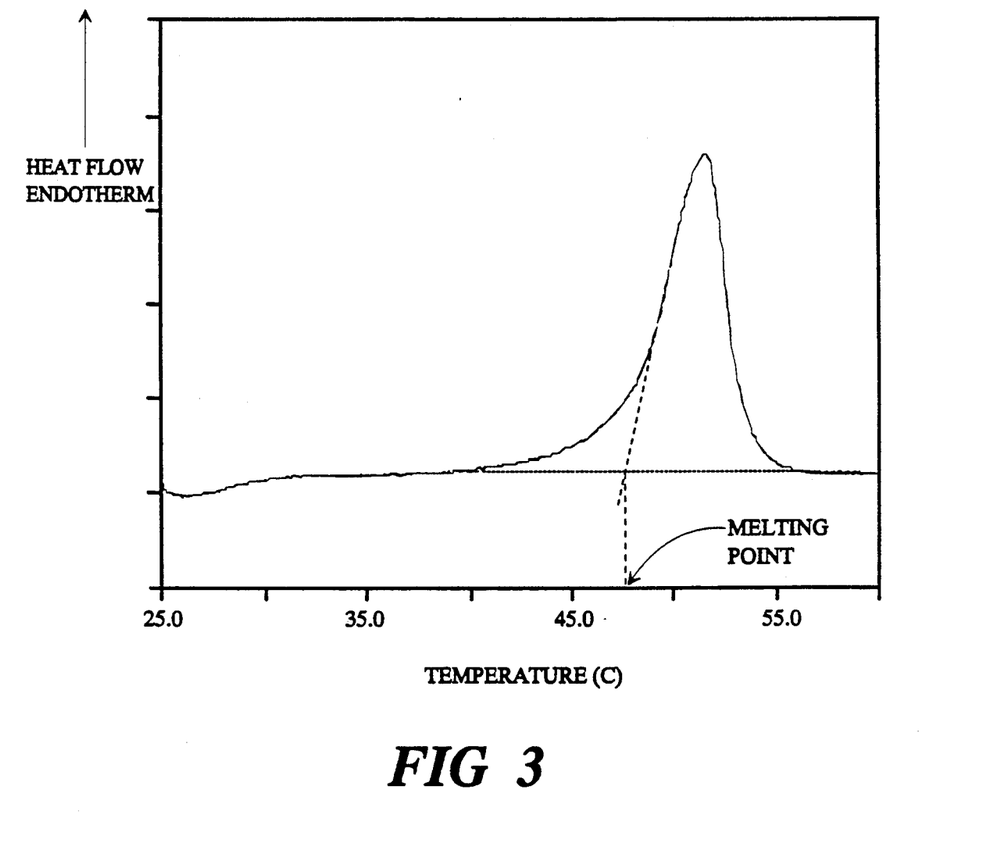
FIG. 3 is a differential scanning calorimetry trace of the orange polymorph of trifluralin.
Figure 4:
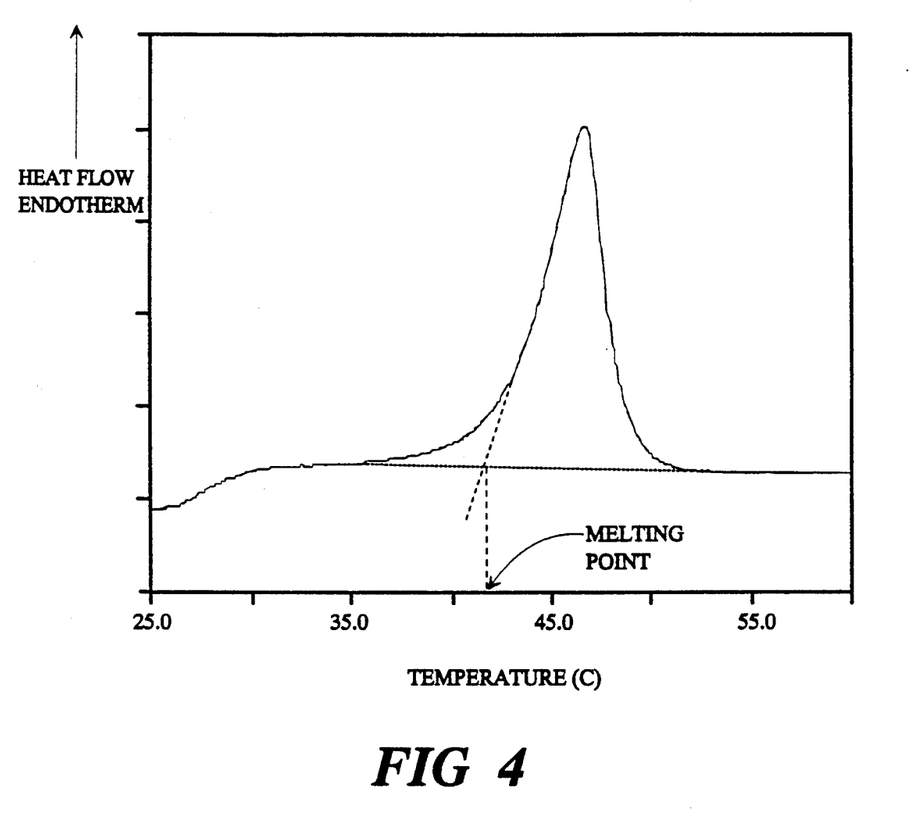
FIG. 4 is a differential scanning calorimetry trace of the yellow polymorph of trifluralin.
Figure 5:
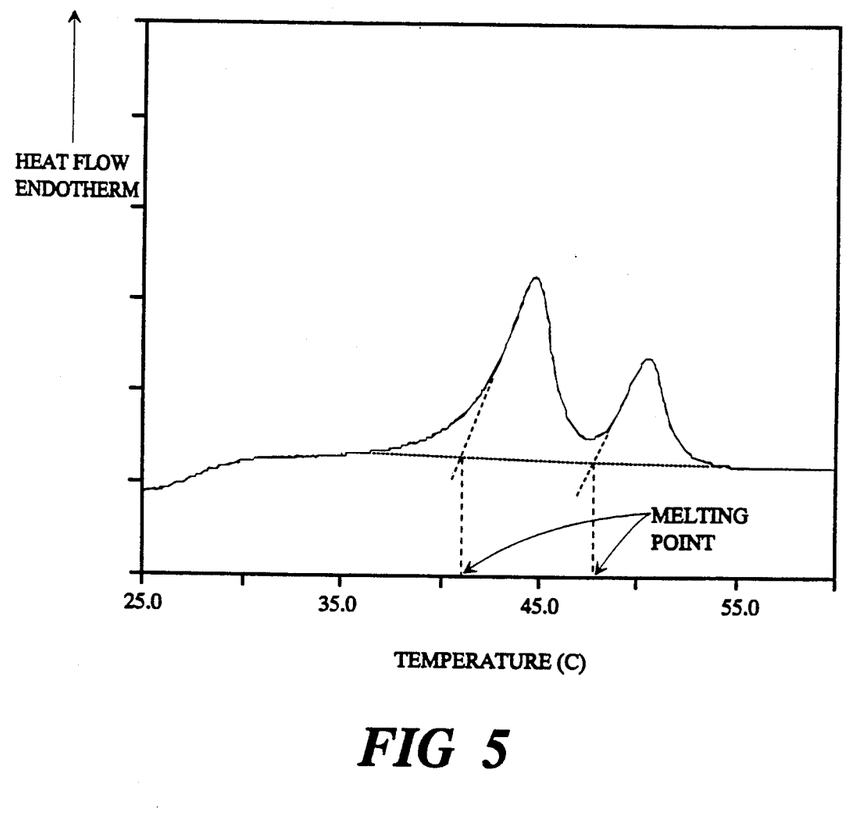
FIG. 5 is a differential scanning calorimetry trace of a mixture of the yellow and orange polymorph of trifluralin.

In addition, FIG. 3 shows the melting point of the orange polymorphic form of trifluralin; FIG. 4 shows the melting point of the yellow polymorphic form of trifluralin; and FIG. 5 shows the relative melting points of a mixture of the yellow and orange polymorphic forms of trifluralin. These traces clearly show the distinctive melting endotherm of the two polymorphic forms of trifluralin.

The low-melting microencapsulation process of the present invention is particularly well suited for use with the above-referenced heat-alterable, polymorphic, agriculturally active materials. Under ambient conditions, the less stable polymorphic form tends to revert to the stable polymorphic form. However, it has been unexpectedly discovered that by microencapsulating the active material in the less stable polymorphic form the active material is preserved and maintained in the less stable polymorphic form. The microencapsulation process therefore provides a mechanism by which the less stable polymorphic form of the active material can be rendered storage stable for relatively long periods of time or at least can be preserved in the less stable polymorphic form until time of use.

It is also an aspect of the present invention that it has been unexpectedly discovered that some of the above-referenced polymorphic active materials, have greater biological activity in the less stable polymorphic form than in the more stable polymorphic form. For example, the yellow polymorphic form of trifluralin displays greater herbicidal activity than does the orange polymorphic form of trifluralin. Some of the less stable polymorphic forms of the active materials also possess enhanced physical properties over the stable polymorphic form in terms of dispersability in water and stability of aqueous dispersions thereof. For example, the yellow polymorphic form of trifluralin possesses better properties of dispersibility in water and storage stability than does the orange polymorphic form of trifluralin.

The low-melting, polymorphic, agriculturally active materials are processed in the low-melting microencapsulation process of the present invention in the same manner as the other low-melting active materials described above. Initially, the low melting, active material is in its most stable polymorphic form. The active material is then heated to a molten state. The molten, active material is then combined with the aqueous solution of the film-forming polymer and the combination is stirred so as to disperse or emulsify the molten active material in the aqueous phase. The resulting emulsion or dispersion is then spray dried so as to microencapsulate the active material. The resulting product is a dry, free-flowing powder or granule.

Following the heating associated with spray drying, the microencapsulated active material will return to ambient temperatures. At ambient temperatures, the active material within the microcapsule will return to the solid phase. Generally, the resolidification of the active material following the melting and the spray drying of the active material converts the active material from the stable polymorph to the less stable polymorph. Therefore, the result of the microencapsulation process is the microencapsulation of the less stable polymorphic form of the active material.

By merely permitting the microcapsules to return to ambient or room temperature (approximately 20° C.), the conversion of the active material from the stable polymorph to the less stable polymorph may not be a complete conversion. Therefore, in order to increase the percentage of conversion to the less stable polymorph, the microcapsules are rapidly cooled following spray drying to a temperature of between approximately −20° and 30° C.; preferably, between approximately −5° and 5° C. Following the cooling step, when the microcapsules are returned to ambient temperatures, the degree of conversion of the active material to the less stable polymorph is improved.

It has further been discovered that the degree of conversion of the active material from the stable polymorph to the less stable polymorph can be improved by subjecting the microcapsules to a prolonged relatively low temperature heat treatment following the cooling step. Accordingly, following the cooling step, the microcapsules can be heated to a temperature above the melting point of the active material; preferably, to a temperature of between approximately 50° and 60° C., for a period of time sufficient to improve the conversion to the less stable polymorph; preferably, between approximately 30 and 90 minutes. The result of this additional heat treatment step is that the degree of conversion of the active material to the less stable polymorph is improved.

In addition to the second heat treatment step, it has been discovered that the degree of conversion of the polymorphic active material can be increased by the use of crystallization initiators or stabilizers. Materials which have been found to help promote the formation (crystallization) of or stabilize and maintain the active material in the less stable polymorphic form include: organic acids and salts, such as Benzoic Acid, Sodium Benzoate, Salicylic Acid; 3-Hydroxybenzoic Acid and 4-Hydroxybenzoic Acid; dinitroanilines, such as N-(1-ethylpropyl)-3,4-dimethyl-2,6-dinitrobenzenamine, 3,5-dinitro-$N^4,N^4$-dipropylsulfanilamide and 2-dipropylamino-3,5-dinitrobenzotrifluroride; and surfactants, such as Polyoxyethylene(2) cetyl ether, Polyoxyethylene (8) stearate, Diethylene glycol monostearate, Polyethylene glycol 400 monostearate, Sorbitan monostearate, Sorbitan monooleate, Sorbitan trioleate, Polyoxyethylene (20) sorbitan monolaurate, Polyoxyethylene (20) sorbitan monooleate and Nonylphenol 4 mole ethoxylate. Materials which have been found to help maintain or stabilize the active material in the less stable polymorphic form include: surfactants, such as Sodium or Calcium dodecylbenzene sulfonate, Tetrasodium N-(1,2-dicarboxyethyl)-N-octadecylsulfosuccinamate, Dioctyl ester of sodium sulfosuccinic acid, Sodium N-Methyl-N-oleoyl taurate, Sorbitan monolaurate, Tetramethyl decynediol and Dodecylphenol-9 mole ethoxylate.

The crystallization initiators can be added to the aqueous phase prior to dispersion or emulsification of the active material therein. Alternately, the crystallization initiators can be added to the molten active material before dispersion or emulsification in the aqueous phase. The amount of the crystallization initiator which is added to the aqueous phase or molten active material is that amount which is effective to promote the formation of the desired polymorph, generally between approximately 0.1% and 10% by weight; preferably, between approximately 0.5% and 2% by weight.

With the use of the crystallization initiators of the present invention, it has been unexpectedly discovered that the less stable polymorphic form of the active material after it has been microencapsulated can be repeatedly temperature cycled through the active materials' melting point and upon cooling to ambient or room temperature will return to the solid, less stable polymorphic form. Such conditions of temperature cycling are often found under typical storage conditions. Therefore, the use of the crystallization initiators of the present invention makes the microencapsulated, less stable, polymorphic, active material more storage stable.

The low-melting active materials which are useful in the present invention include dinitroaniline herbicides. It is well known that the typical manufacturing process for dinitroanilines produces nitrosamines as a side reaction product. Nitrosamines, of course, are recognized carcinogens. Current government regulations place strict limits on the permissible amounts of nitrosamines which can be present in herbicides. It has been unexpectedly discovered that the use of the microencapsulation process of the present invention when encapsulating active materials which initially contain nitrosamines as an impurity reduces the level of nitrosamines in the microencapsulated product.

Specifically, a dinitroaniline herbicide, such as trifluralin, may contain as much as 50 parts per million of nitrosamine as an impurity from the manufacturing process. Generally, heating dinitroaniline herbicides increases nitrosamine content. Surprisingly, however, by microencapsulating such trifluralin using the low-melting microencapsulation process of the present invention, the trifluralin which has been microencapsulated by said process contains reduced levels of nitrosamine contamination compared to the original trifluralin material before being microencapsulated by said process. Although the mechanism by which the nitrosamines are removed from the active material is not understood, it is believed that the removal of water from the microcapsules during the spray drying process steam distills the nitrosamines from the microcapsule, thereby reducing the level of nitrosamines remaining in the microcapsule.

The present invention also includes a process for microencapsulating high-melting active materials. In the practice of the high-melting microencapsulation process, the same aqueous solutions of film-forming polymers are used as can be used with the low-melting microencapsulation process described above. However, since the high-melting active materials are solid at the temperatures involved in the process, it is necessary to grind the high-melting active material to a relatively small particle size. Generally speaking, the high-melting active material should be ground to a particle size of between approximately 0.1 and 10 microns. The particular equipment used to grind the high-melting active material is not critical and several suitable types of equipment are well known to those skilled in the art.

After the high-melting active material has been ground to an appropriate particle size, it is combined with the aqueous solution of the film-forming polymer. The aqueous solution is agitated during the addition of the ground active material so that the active material is completely and uniformly dispersed within the aqueous solution. Agitation is maintained until the resulting dispersion is spray dried.

The dispersion of the ground, high-melting active material in the aqueous solution of the film-forming polymer is then spray dried in the same manner as in the low-melting microencapsulation process.

Proper packaging of the spray-dried encapsulated active material provides important benefits. In general, any package, such as bottles, jugs, bags, and the like may be used as long as a sufficient moisture barrier is obtained, to prevent caking of the product due to absorption of moisture from the air on storage.

For example, the desired polymorphic form of trifluralin may be produced by rapid cooling before or after packaging. If necessary, any undesired polymorphic material present in the spray-dried product can be removed by re-melting prior to rapid cooling to a temperature between −20° C. and 30° C. Heating can be accomplished by any suitable means, such as oven or tray heating, fluid bed heating and the like. The product may be packaged before or after the heating and cooling steps, but final sealing of the package prior to the cooling step is preferred.

Alternately, a high yield of the desired polymorph can be attained by slow cooling to a temperature between −20° C. and 30° C. In this method, the product can be heated if necessary to eliminate any undesired polymorph, but the package should be sealed prior to slow cooling of the spray-dried product. This process results in a high yield of the desired polymorph.

Surprisingly, trifluralin in the spray-dried product prepared and packaged by the above method can be stored at room temperatures above its melting point without harming its physical properties or producing the undesired polymorph.

The microencapsulated active material in accordance with the present invention is a dry, free flowing powdery substance. The microencapsulated active material can be readily dispersed in water to form a sprayable composition. When the microencapsulated active material is added to water, the water-soluble, film-forming polymer which forms the wall of the microcapsule readily dissolves. The result is an aqueous dispersion of the active material. The aqueous dispersion of the active material can then be used in a conventional manner, such as by spraying an area to be treated.

With respect to the less stable polymorphic form of active materials, such as the yellow polymorphic form of trifluralin, the present invention provides a means of rendering the less stable polymorphic form relatively storage stable. Then, when desired, an aqueous dispersion of the less stable polymorphic form of the active material can be prepared and applied to an area to be treated. Specifically, in the case of the yellow polymorphic form of trifluralin, an aqueous dispersion of the yellow trifluralin can be prepared and applied to control weeds. It has been unexpectedly discovered that the less stable polymorphic forms of the active materials, specifically the yellow polymorphic form of trifluralin, possess greater biological activity than the more stable polymorphic form. Furthermore, aqueous dispersions of the less stable polymorphic active material tend to be more stable than aqueous dispersions of the more stable polymorphic active material.

The following examples are illustrative of the present invention and are not intended to limit the scope of the invention as set forth in the appended claims. All temperatures are in degrees Celsius and all percentages are by weight unless otherwise stated.

EXAMPLE 1

157.0 g. of water is heated and maintained at 60° C. To this is slowly added 15.7 g. of partially hydrolyzed polyvinyl alcohol (PVA) with a degree of hydrolysis of 87-89% and a molecular weight of 10,000-30,000. The mixture is agitated until the PVA is completely dissolved. To this aqueous solution is then added 0.1 g. of sodium dioctyl sulfosuccinate. Further stirring is carried out, with the temperature of the solution being maintained at 60° C. 84.2 g. of technical grade trifluralin (a,a,a-trifluro-2,6-dinitro-N,N-dipropyl-p-toluidine) is melted by heating to 60° C., is then added to the aqueous solution and emulsified with a high shear homogenizer. The emulsion particle size is further reduced by passing the emulsion through a pressure valve homogenizer until an average size of 1.1 microns is achieved.

The emulsion is then spray dried at an inlet air temperature of 180° C., and an outlet air temperature of 104° C. A laboratory type spray dryer is used with two fluid nozzle atomization.

60 g. of a dry free-flowing powder is obtained with a particle size of 20-25 microns. The product is then packaged in foil laminate bags. This material is heated to 55°-60° C. to assure melting of the undesired polymorph and then rapidly cooled to 0° C. to effect the solidification of the trifluralin and produce the desired polymorphic form. The presence of the yellow polymorph is confirmed by the use of differential scanning calorimetry (DSC) which exhibits a distinctive melting endotherm occurring at 41°-43° C., the melting point of the yellow form.

The product exhibits excellent properties on dilution in water, wetting almost instantly, producing a stable suspension on standing.

The finished product contains 80% by weight of trifluralin and maintains its biological and physical properties on storage at both ambient and elevated temperatures.

EXAMPLE 2

157 g. of water is heated to 60° C. and, under moderate agitation 15.7 g. of partially hydrolyzed polyvinyl alcohol having a degree of hydrolysis of 87-89% and a molecular weight of 10,000 to 30,000 is added thereto. 83.5 g. of technical grade trifluralin is melted, and heated to 60° C. 0.84 g of Toximul T-814 is added to the molten trifluralin, and stirred until a homogeneous mixture is obtained. The molten mixture is added to the polymer solution and agitated with a high shear homogenizer until a uniform dispersion is obtained. A pressure valve emulsifier is then used to reduce the droplet particle size to 1.0 micron.

The emulsion thus formed is spray dried, using a laboratory spray dryer fitted with a two fluid nozzle atomizer, at an inlet air temperature of 180° C., and a outlet air temperature of 106° C. A free-flowing powder is obtained with a particle size of 20-25 microns. The powder is then packaged in foil laminate bags.

The powder thus obtained is heated to 55°-60° C. to assure melting of the undesired polymorph then rapidly cooled to 0° C. so that the trifluralin technical solidifies as the yellow polymorph. The product has excellent properties on dilution with water, wetting rapidly to produce a stable suspension on standing. It maintains good physical and chemical properties on storage at both ambient and elevated temperatures.

EXAMPLE 3

255 g. of water is heated and maintained at 65° C., and to this is slowly added 25.5 g. partially hydrolyzed polyvinyl alcohol with a degree of hydrolysis of 87%-89% and a molecular weight of 10,000-30,000. The mixture is agitated until the PVA is completely dissolved. Further stirring is carried out with the temperature being maintained at 65° C.

74.5 g. of technical grade ioxynil (4-hydroxy-3,5-diiodobenzonitrile) as the octanoate ester is melted by heating to 65° C., is added to the aqueous solution and is emulsified with a high shear homogenizer. The emulsion particle size is further reduced by passing the emulsion through a pressure valve homogenizer until an average particle size of 1.2 microns is achieved.

The emulsion is then spray dried at an inlet air temperature of 180° C. and an outlet air temperature of 106° C. A laboratory type spray dryer is used with two-fluid nozzle atomization.

50 g. of a dry free-flowing powder is obtained with a particle size of 20-25 microns. The finished product contains predominantly the low-melting polymorph (melting point 52° C.) with only a few percent of the higher-melting polymorph (melting point 57° C.).

The product exhibits excellent properties on dilution in water, wetting almost instantly, producing a stable suspension on standing.

The finished product contains 70% by weight of ioxynil octanoate and maintains its physical properties on storage.

EXAMPLE 4

232 g. of water is heated to 60° C. and, under moderate agitation, 23.2 g. of partially hydrolyzed polyvinyl alcohol, having a degree of hydrolysis of 87-89% and a molecular weight of 10,000-30,000 is added. 76.8 g. of technical grade bromoxynil (3,5-dibromo-4-hydroxybenzonitrile) as the octanoate ester is melted by heating to 60° C. The molten technical material is added to the polymer solution and agitated with a high shear homogenizer until a uniform dispersion is obtained. A pressure valve homogenizer is then used to reduce the droplet particle size to 1.0 micron.

The emulsion thus formed is spray dried, using a laboratory spray dryer fitted with a two fluid nozzle atomizer, an inlet air temperature of 180° C. and an outlet air temperature of 106° C. A free-flowing powder is obtained with a particle size of 10-25 microns.

The product melts at 41.7° C. as determined by DSC. The finished product contains 70% by weight of bromoxynil octanoate.

EXAMPLE 5

184 g. of water is heated to 60° C. and, under moderate agitation, 18.4 g. of partially hydrolyzed polyvinyl alcohol, having a degree of hydrolysis of 87%-89% and a molecular weight of 10,000-30,000 is added. 31.6 g. of technical grade pendimethalin [N-(1-ethylpropyl)-3,4-dimethyl-2,6-dinitrobenzenamine] is melted by heating to 60° C. The molten technical material is added to the polymer solution and agitated with a high shear homogenizer until a uniform dispersion is obtained. A pressure valve homogenizer is then used to reduce the droplet particle size to 1.3 microns.

The emulsion thus formed is spray dried, using a laboratory spray dryer fitted with a two-fluid nozzle atomizer, at an inlet air temperature of 180° C., and an outlet air temperature of 106° C. A free-flowing powder is obtained with a particle size of 20-25 microns.

The finished product contains 60% by weight of pendimethalin and maintains its physical properties on storage at both ambient and elevated temperatures. The finished product contains only the polymorph melting at 53.2° C., as determined by DSC. The product has excellent properties on dilution with water, wetting rapidly to produce a stable suspension on standing.

EXAMPLE 6

314.0 g. of water is heated and maintained at 60° C. To this is slowly added 31.4 g. of polyvinylpyrrolidone (PVP) having an average molecular weight of approximately 24,000. The mixture is agitated until the PVP is completely dissolved. To this is added 1.68 g. of sodium dodecylbenzene sulfonate. Further stirring is carried out with the temperature being maintained at 60° C.

166.92 g. of trifluralin is melted by heating to 60° C. The molten trifluralin is then added to the aqueous solution and emulsified with a high shear homogenizer. The emulsion particle size is further reduced by passing the emulsion through a pressure valve homogenizer until the average particle size of 1.1 microns is achieved.

The emulsion is then spray dried at an inlet air temperature of 180°-181° C. and an air outlet temperature of 106°-112° C. A dry free-flowing powder is obtained with a particle size of 20-25 microns. This product is sealed in a bag and placed in a hot air oven at 55° C. for a period of 1 hour. The polyethylene bag is then foil packed and left at room temperature for 10 days. DSC analysis reveals that the microcapsules contain 87.2% of the yellow trifluralin polymorph and no measurable percentage of the orange polymorph.

EXAMPLE 7

The same process as described above in Example 6 is followed except the PVP has an average molecular weight of approximately 40,000. DSC analysis reveals that the microcapsules contain 77.2% of the yellow trifluralin polymorph and no measurable percentage of the orange polymorph.

EXAMPLE 8

366.1 g. of water is heated to 60° C. and stirred while 1.95 g. sodium dodecylbenzene sulfonate and 29.25 g. of 87-89% hydrolyzed polyvinyl alcohol (molecular weight 10,000-30,000) are added and dissolved. 195 g. of molten trifluralin are then added with high shear to produce an emulsion. The emulsion particle size is further reduced by passing the emulsion through a pressure valve homogenizer to produce an emulsion particle size of 1.5 microns.

The emulsion is then spray dried at an inlet air temperature of 188° C. and an outlet air temperature of 107° C., yielding 30 g. of a free-flowing powder with a particle size between 10 and 25 microns. When cooled from 60° C. to room temperature and held at room temperature for 7 days, the desired yellow polymorph is produced in excess of 95%, based on DSC analysis.

EXAMPLE 9

557.1 g of water are heated to 60° C. and stirred while 49.4 g. of 87-89% hydrolyzed polyvinyl alcohol (molecular weight 10,000-30,000) are slowly added. When the PVA is completely dissolved, 0.3 g. of sodium dioctyl sulfosuccinate is added.

Separately, 240.0 g. of trifluralin are melted and held at 60° C. with stirring while 0.3 g. of 3-hydroxy benzoic acid is added and dissolved. This solution is then added to the PVA solution and emulsified with a high shear homogenizer to produce an emulsion particle size of 1.1 microns.

The emulsion is then spray dried in a laboratory type spray dryer at an air inlet temperature of 187° C. and air outlet temperature of 105° C. using two-fluid nozzle atomization. 49.3 g. of a free flowing powder are produced with a particle size of 15-30 microns.

EXAMPLE 10

The biological activity of the yellow polymorphic form of trifluralin having a melting point of approximately 41°-43° C. is compared with the biological activity of the orange polymorphic form of trifluralin having a melting point of approximately 46°-49° C. Aqueous dispersions of the orange polymorph, the yellow polymorph and a control are incorporated with soil at a rate of 0.5 pounds active ingredient per acre. The control is made from a commercially available emulsifiable trifluralin concentrate.

TABLE 2

| % Control[1] (at 0.5 lbs.a.i. per acre application rate[2]) | | | |
|---|---|---|---|
| | Barnyardgrass[3] | Crabgrass[4] | Pigweed[5] |
| EC[6] | 39 | 41 | 34 |
| Orange Polymorph | 53 | 56 | 50 |
| Yellow Polymorph | 86 | 82 | 58 |

[1] % control 14 days after application. 0 = no control, 100 = complete
[2] Application to sandy loam soil
[3] *Echinochloa crusgalli*
[4] *Digitaria sanguinalis*
[5] *Amaranthus retroflexus*
[6] Commercially available emulsifiable concentrate (Treflan, Elanco)

EXAMPLE 11

Another aspect of the invention is the unexpected reductions of the unwanted nitrosamine contaminant that is formed during the manufacture of dinitroaniline herbicides, such as trifluralin. Analysis of the active ingredient before and after spray drying according to the invention reveals significant reduction of the nitrosamine contaminant, as shown in Table 3.

TABLE 3

| | Nitrosamine Concentration (ppm) in trifluralin | |
|---|---|---|
| | Sample A | Sample B |
| Before Spray Drying | 1.00 | 0.15 |
| After Spray Drying | <0.05* | <0.05* |

*Below detection limit

EXAMPLE 12

366 g. of water and 195 g. of technical grade chlorothalonil (tetrachloroisophthalonitrile) are added to a laboratory mill and ground to a median particle size of 2–4 microns, while the temperature of the dispersion is maintained at about 70° C. for about four hours. 1.95 g. of sodium dodecylbenzene sulfonate and 37.1 g. of polyvinyl alcohol having a degree of hydrolysis of 87–89 percent and a molecular weight of 10,000 to 30,000 are then added to the dispersion and dissolved.

The dispersion is then spray dried at an inlet air temperature of 200° C. and an outlet air temperature of 105° C., using a laboratory-type spray drier with two-fluid nozzle atomization. A free-flowing powder with a particle size of about 15–35 microns is produced which contains the higher melting polymorph of chlorothalonil, melting at 251.5° C. This polymorph is known as type I, and is characterized by superior properties.

EXAMPLE 13

The procedure of Example 4 is followed except that the following materials having the following melting points are separately substituted for the bromoxynil octanoate as the agriculturally active material:

| Active Material | Melting Point |
|---|---|
| I. Diclofop-methyl | 39° |
| II. Alachlor | 39° |
| III. Senoxan | 36° |
| IV. Oxyfluorofen | 65° |
| V. Flamprop-methyl | 81° |
| VI. Cypermethrin | 60° |
| VII. Ethalfluralin | 57° |
| VIII. Benfluralin | 65° |
| IX. Acephate | 82° |
| X. Methomyl | 78° |
| XI. Imazalil | 50°. |

Heating of the active materials is carried out as in Example 4 except that the temperature is adjusted to a temperature above the melting point of the active material.

Each of the above-referenced active materials is microencapsulated in the polyvinyl alcohol by spray drying. The resulting products are dry, free-flowing powders or granules of the encapsulated active materials listed above.

EXAMPLE 14

The procedure of Example 12 is followed except that the following materials having the following melting points are separately substituted for the chlorothalonil as the agriculturally active material:

| Active Material | Melting Point |
|---|---|
| I. Oxamyl | 102° |
| II. Deltamethrin | 98° |
| III. Metribuzin | 125° |
| IV. Oryzalin | 141° |
| V. Atrazine | 174° |
| VI. Propanil | 91° |
| VII. Quizalofop-ethyl | 91°. |

The products of the spray drying process are dry free-flowing powders of the above-referenced active materials microencapsulated in polyvinyl alcohol.

EXAMPLE 15

The procedure of Example 6 is followed except the following water-soluble, film forming polymers are separately substituted for the polyvinylpyrrolidone:
I. Sodium Carboxymethylcellulose
II. Gum Acacia
III. Poly (Acrylic Acid)
IV. Casein
V. Hydrolyzed Maltodextrin (5 Dextrose equivalent)
VI. Modified starch
VII. Starch
VIII. Polyacrylamide
IX. Hydroxyethylcellulose.

The products of the spray drying process are dry free-flowing powders of trifluralin microencapsulated in the above-referenced polymers.

EXAMPLE 16

The procedure of Example 9 is followed except that the following crystallization initiators are separately substituted for the 3-hydroxy benzoic acid:
I. 3,5-dinitro-N[4],N[4]-dipropylsulfanilamide
II. N-(1-ethylpropyl)-3,4-dimethyl-2,6-dinitrobenzenamine.

The spray drying process produces a free flowing powder.

EXAMPLE 17

The procedure of Example 8 is followed except that the following crystallization initiators are separately substituted for the sodium dodecylbenzene sulfonate:
I. Sodium N-methyl-N-oleyl taurate
II. Polyoxyethylene (20) sorbitan monostearate
III. Polyoxyethylene (2) cetyl ether
IV. Polyoxyethylene (8) stearate
V. Sorbitan monooleate
VI. Calcium dodecylbenzene sulfonate.

The products of the spray drying are dry free flowing powders of the desired yellow polymorph of trifluralin produced in excess of 95%, based on DSC analysis.

EXAMPLE 18

The improved physical properties of the yellow polymorphic form of trifluralin compared to the orange polymorphic form of trifluralin is shown in Table 4 below:

TABLE 4

| % Yellow Solid | % Orange Solid | % Super Cooled Liquid | Suspensability | Wetting Time |
|---|---|---|---|---|
| 0 | 96 | 4 | 32 | >60 Secs |
| 76 | 6 | 18 | 80 | <10 Secs |

The foregoing data clearly shows that the yellow polymorphic form of trifluralin possesses improved properties of dispersability in water compared to the orange polymorphic form of trifluralin.

We claim:

1. A method of controlling weeds comprising the steps of:
    combining with water to form an aqueous suspension a dry herbicidal composition having improved wettability, dispersibility and suspensibility consisting essentially of trifluralin having a polymorphic form characterized by a yellow color and a melting point of approximately 41°–43° C., said herbicidal composition being microencapsulated in a water-soluble microcapsule, said composition being substantially free of a solvent for said trifluralin; and
    applying an effective amount of said aqueous suspension to soil.

2. The method of claim 1, wherein said herbicidal composition further includes a stabilizing amount of a compound selected from the group consisting of benzoic acid, sodium benzoate, salicylic acid, 3-hydroxybenzoic acid, 4-hydroxybenzoic acid and mixtures thereof.

3. The method of claim 1, wherein said herbicidal composition further includes a stabilizing amount of a compound selected from the group consisting of N-(1-ethylpropyl)-3,4-dimethyl-2,6-dinitrobenzenamine; 3,5-dinitro-$N^4,N^4$-dipropyl-sulfanilamide, 2-dipropylamino-3, 5-dinitrobenzotrifluoride and mixtures thereof.

4. The method of claim 1, wherein said herbicidal composition further includes a stabilizing amount of a compound selected from the group consisting of sodium dodecylbenzene sulfonate, tetrasodium N-(1, 2-dicarboxyethyl)-N-octadecylsulfosuccinamate, dioctyl ester of sodium sulfosuccinic acid, sodium N-methyl-N-oleoyl taurate, sorbitan monolaurate, tetramethyl decynediol, dodecylphenol-9 mole ethoxylate and mixtures thereof.

5. The method of claim 1, wherein said herbicidal composition further includes a stabilizing amount of a compound selected from the group consisting of tetramethyl decynediol, polyoxyethylene (20) sorbitan monostearate and polyoxyethylene (20) sorbitan trioleate and mixtures thereof.

6. The method of claim 1, wherein said herbicidal composition further includes a stabilizing amount of a compound selected from the group consisting of polyoxyethylene (2) cetyl ether, polyoxyethylene (8) stearate, diethylene glycol monostearate, polyethylene glycol 400 monostearate, sorbitan monostearate, sorbitan monooleate, sorbitan trioleate, polyoxyethylene (20) sorbitan monolaurate, polyoxyethylene (20) sorbitan monooleate, nonylphenol 4 mole ethoxylate and mixtures thereof.

7. The method of claim 1, wherein said herbicidal composition further includes a stabilizing amount of sodium dodecylbenzene sulfonate.

* * * * *